US007569218B2

(12) United States Patent
Weiner et al.

(10) Patent No.: US 7,569,218 B2

(45) Date of Patent: Aug. 4, 2009

(54) COMPOSITIONS FOR AND METHODS OF USING HERPES SIMPLEX VIRUS GLYCOPROTEIN D TO SUPPRESS IMMUNE RESPONSES

(75) Inventors: David B. Weiner, Merion Station, PA (US); Jeong-Im Sin, Daegu (KR)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 608 days.

(21) Appl. No.: 10/333,802

(22) PCT Filed: Jul. 27, 2001

(86) PCT No.: PCT/US01/23648

§ 371 (c)(1), (2), (4) Date: Jul. 29, 2003

(87) PCT Pub. No.: WO02/10410

PCT Pub. Date: Feb. 7, 2002

(65) Prior Publication Data

US 2004/0014705 A1 Jan. 22, 2004

Related U.S. Application Data

(60) Provisional application No. 60/221,025, filed on Jul. 27, 2000.

(51) Int. Cl.
*A61K 48/00* (2006.01)

(52) U.S. Cl. .................................................... 424/93.2

(58) Field of Classification Search ................. 424/93.2
See application file for complete search history.

(56) References Cited

U.S. PATENT DOCUMENTS

| | | | | |
|---|---|---|---|---|
| 4,235,871 | A | 11/1980 | Papahdjopoulos et al. | |
| 4,241,046 | A | 12/1980 | Papahdjopoulos et al. | |
| 4,394,448 | A | 7/1983 | Szoka et al. | |
| 4,945,050 | A | 7/1990 | Sanford et al. | |
| 5,036,006 | A | 7/1991 | Sanford et al. | |
| 5,459,127 | A | 10/1995 | Felgner et al. | |
| 5,580,859 | A | 12/1996 | Felgner et al. | |
| 5,583,028 | A | 12/1996 | Paoletti | |
| 5,589,466 | A | 12/1996 | Felgner et al. | |
| 5,593,972 | A | 1/1997 | Weiner et al. | |
| 5,614,503 | A | 3/1997 | Chaudhary et al. | |
| 5,622,712 | A | 4/1997 | Eppstein et al. | |
| 5,676,954 | A | 10/1997 | Brigham | |
| 5,703,055 | A | 12/1997 | Felgner et al. | |
| 5,707,618 | A | 1/1998 | Armentano et al. | |
| 5,739,118 | A | 4/1998 | Carrano et al. | |
| 5,756,283 | A | 5/1998 | Wilson et al. | |
| 5,837,533 | A | 11/1998 | Boutin | |
| 5,955,088 | A | 9/1999 | Ghiasi et al. | |
| 5,958,895 | A | 9/1999 | Pachuk et al. | |
| 6,290,949 | B1 * | 9/2001 | French et al. | 424/93.2 |
| 6,355,247 | B1 * | 3/2002 | Selby et al. | 424/188.1 |

FOREIGN PATENT DOCUMENTS

| | | | |
|---|---|---|---|
| WO | WO90/11092 | | 10/1990 |
| WO | WO93/17706 | | 9/1993 |
| WO | WO 96/11277 | * | 4/1996 |
| WO | WO99/43839 | | 9/1999 |

OTHER PUBLICATIONS

Zheng et al. Vaccine, 11:1191-1198, 1993.*

Kafri et al. PNAS 95: 11377-11382, 1998.*

Sin, J.I., et al., "Enhancement of protective humoral (Th2) and cell-mediated (Th1) immune response against herpes simplex virus-2 through codelivery of granulocyte-macrophage colony-stimulating factor expression cassettes," Eur. J. Immunol. (1998) 28: 3530-3540.

Ruitenberg, K.M., et al., "A prime-boost immunization strategy with DNA and recombinant baculovirus-expressed protein enhances protective immunogenicity of glycoprotein D of equine herpesvirus 1 in naive and infection-primed mice," Vaccine (2000) 18:1367-1373.

Zhu, et al., "A chimeric protein comprised of bovine herpesvirus type 1 glycoprotein D and bovine interleukin-6 is secreted by yeast and possesses biological activities of both molecules," Vaccine (1999) 17:269-282.

(Continued)

*Primary Examiner*—Brian Whiteman

(74) *Attorney, Agent, or Firm*—Pepper Hamilton LLP

(57) ABSTRACT

Methods of delivering a desired polypeptide to an individual are disclosed. The methods comprise administering to the individual an immunogenic vector comprising a nucleic acid encoding the desired polypeptide operably linked to regulatory elements in combination with one or more of gD protein, a function fragment of gD protein, a nucleic acid encoding gD protein operably linked to regulatory elements, or a nucleic acid encoding a functional fragment of gD protein operably linked to regulatory elements. Compositions comprising an immunogenic vector that comprises a nucleic acid encoding the desired polypeptide operably linked to regulatory elements; and one or more of gD protein, a function fragment of gD protein, a nucleic acid encoding gD protein operably linked to regulatory elements, or a nucleic acid encoding a functional fragment of gD protein operably linked to regulatory elements are disclosed. Methods for inhibiting an undesirable immune response in an individual are disclosed.

3 Claims, 1 Drawing Sheet

OTHER PUBLICATIONS

Sin, et al., "In vivo modulation of vaccine-induced immune responses toward a Th1 phenotype increases potency and vaccine effectiveness in a Herpes simplex virus type 2 mouse model," J. Virol. (1999) 73:501-509.

Sin, et al., "IL-12 gene as a DNA vaccine adjuvant in a Herpes mouse model: IL-12 enhances Th1-type CD4+ T cell-mediated protective immunity against Herpes simplex virus-2 challenge," J. Immunol. (1999) 162:2912-2921.

Flo, et al., "Modulation of the immune response to DNA vaccine by co-delivery of costimulatory molecules," Immunology (2000) 100:259-267.

Hazama, et al., "Adjuvant-independent enhanced immune responses to recombinant herpes simple virus-type 1 glycoprotein D by fusion with biologically active interleukin-2," Vaccine (1993) 11:629-636.

Liljeqvist and Stahl, "Production of recombinant subunit vaccines: protein immunogens, live delivery systems and nucleic acid vaccines," J. Biotechnol. (1999) 1-33.

Kim and Weiner, "Development of multicomponent DNA vaccination strategies against HIV," Curr. Opin. Mol. Therap. (1998) 1:43-49.

* cited by examiner

COMPOSITIONS FOR AND METHODS OF USING HERPES SIMPLEX VIRUS GLYCOPROTEIN D TO SUPPRESS IMMUNE RESPONSES

CROSS REFERENCE TO RELATED APPLICATIONS

This application is a U.S. National Phase Application of PCT International Application PCT/US01/23648.

The present application claims priority to U.S. provisional application Ser. No. 60/221,025 filed Jul. 27, 2000.

FIELD OF THE INVENTION

The present invention relates to methods of inhibiting anti-viral response, to improved gene delivery methods, to methods of treating individuals who have autoimmune diseases and to methods of treating individuals who have diseases, disorders and conditions associated with inflamation. The present invention relates to pharmaceutical compositions useful in such methods. The present invention relates to improved gene therapy vectors and compositions which comprise HSV gD or a gene encoding the same, and methods of making and using the same. The present invention relates to methods for delivering polypeptides to individuals while inhibiting the cellular immune response against the vector which contains the nucleic acid encoding the desired polypeptide.

BACKGROUND OF THE INVENTION

One promise of gene therapy is the ability to correct genetic defects responsible for disease by the addition to an individual of functional genetic material as well as the ability to deliver therapeutic proteins using genetic material that encodes such proteins. There is a great deal of activity in the development of protocols for treating diseases and disorders by administering a nucleic acid which codes for a polypeptide that is either missing or defective in an individual. Another promise of gene therapy is as an alternative and improved means to deliver therapeutically important proteins to individuals in need of such proteins. The discovery of proteins with therapeutically important functions has led to new treatments for many diseases and disorders and the application of gene therapy to deliver such proteins is also the subject of much interest.

Among the strategies for delivering genetic material, the use of immunogenic vectors, most commonly viral vectors, capable of infecting the individual's cells is the one of the most widely employed methodologies. Essentially, genetic material that encodes desired proteins, whether they be functional forms of defective genes responsible for disease or coding sequences for therapeutically useful proteins, is incorporated into the genome of a vector which has the ability to infect cells of the individual or otherwise deliver the genetic material to cells of the individual.

Adenovirus, adenovirus associated virus (AAV), vaccinia virus, and simian virus 4 (SV40) are just a few of the many viruses used to make viral vectors for gene therapy. In some cases, the viral vectors are selected for their ability to infect specific tissue to which delivery of the genetic material is desired. In some cases, the viral vectors are selected because they are attenuated and cause serious limited infections to the individual without significant pathology.

One of the major problems associated with gene therapy protocols that employ immunogenic vectors is that an immune response against the vector is induced in the individual who is administered the vector. The immune response targets the vector including cells which are infected by the vector. The destruction of cells which are infected by the vector reduces the efficacy of the treatment. Further, immune responses induced against the vectors limit the effectiveness of subsequent doses of the same gene therapeutic composition or other gene therapeutic compositions which use the same vector because the immune system of the individual will recognize the vector from the subsequent doses of the same gene therapeutic composition or other gene therapeutic compositions which use the same vector and mount an immune response similar to the manner in which a vaccine protects the individual from subsequent exposure to a pathogen.

There are two branches to the immune system. The humoral branch of the immune system involves antibodies which are secreted by B lymphoid cells and recognize specific antigens. Binding of antibodies to specific antigens inactivates the antigen. Antibodies may also bind to the antigen and activate other immune cells which destroy the bound antigen.

The cellular branch of the immune system involves specific cell types which recognize and destroy cells which display "foreign" antigens. Cytotoxic T cells (also referred to as cytotoxic T lymphocytes or CTLs) are an example of cells in the cellular branch of the immune system. CTLs recognize fragments of peptides which are displayed on the plasma membrane surface bound to major histocompatibility complex molecules (MHCs). Cells that display a peptide which is "foreign" elicit a cellular immune response. Cytotoxic T cells then destroy the cell displaying foreign peptide fragments.

When a patient undergoes an organ or cell transplant or a tissue graft, the patient's immune system will recognize the donor organ, cells or tissue as "foreign" and mount an immune response against the donor organ, cells or tissue. Immunosuppressive drugs are used to down modulate the patient's immune response and prevent rejection.

In autoimmune disease, the immune system attacks "self" antigen. Some autoimmune diseases are T cell mediated. Examples of T cell mediated autoimnmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Other autoimmune diseases are B cell mediated. Examples of B cell mediated autoimmune diseases are Lupus (SLE), Grave's disease, myasthenia gravis, autoimmune hemolytic anemia, autoimmune thrombocytopenia, asthma, cryoglobulinemia, primary biliary sclerosis and pernicious anemia. In both types, an immune response is directed at the body's own antigens. Autoimmune diseases may be treated by suppressing immune responses.

There remains a need for improved gene therapy vectors, compositions and methods which can be used to increase safety and efficacy. There remains a need for improved gene therapy vectors, compositions and methods which can reduce or elimnate the immune response against the viral vector which limits the ability to expose the individual to subsequent doses of the therapeutic or other therapeutics or vaccines employing the same vector. There is a further need for methods for suppressing immune responses associated with cell organ, cell and tissue transplants. There is a need for methods for delivering polypeptides to individuals while inhibiting the cellular immune response against the vector which encodes the desired polypeptide. There is a further need for methods for modulating immune responses associated with inflammatory and autoimmune diseases and disorders.

SUMMARY OF THE INVENTION

The present invention relates to methods of delivering a desired polypeptide to an individual. The methods comprise administering to the individual an immunogenic vector comprising a nucleic acid encoding the desired polypeptide operably linked to regulatory elements in combination with one or more of gD protein, a functional fragment of gD protein, a nucleic acid encoding gD protein operably linked to regulatory elements, or a nucleic acid encoding a functional fragment of gD protein operably linked to regulatory elements.

The present invention relates to compositions comprising an immunogenic vector that comprises a nucleic acid encoding the desired polypeptide operably linked to regulatory elements; and one or more of gD protein, a functional fragment of gD protein, a nucleic acid encoding gD protein operably linked to regulatory elements, or a nucleic acid encoding a functional fragment of gD protein operably linked to regulatory elements.

The present invention relates to methods for inhibiting an undesirable immune response in an individual. The methods comprise administering to the individual in an amount sufficient to inhibit an undesirable immune response one or more of gD protein, a function fragment of gD protein, a nucleic acid encoding gD protein operably linked to regulatory elements, or a nucleic acid encoding a functional fragment of gD protein operably linked to regulatory elements.

The present invention relates to methods for treating an individual who is about to undergo, is undergoing or has undergone an organ, tissue or cell transplant procedure to prevent rejection and any graft versus host disease associated therewith. The methods comprise administering to the individual in an amount sufficient to down modulate immune responses in the individual, one or more of gD protein, a function fragment of gD protein, a nucleic acid encoding gD protein operably linked to regulatory elements, or a nucleic acid encoding a functional fragment of gD protein operably linked to regulatory elements.

The present invention relates to methods for treating an individual who has an autoimmune disease. The methods comprise administering to the individual in an amount sufficient to down modulate immune responses in the individual, one or more of gD protein, a function fragment of gD protein, a nucleic acid encoding gD protein operably linked to regulatory elements, or a nucleic acid encoding a functional fragment of gD protein operably linked to regulatory elements.

DESCRIPTION OF PREFERRED EMBODIMENTS OF THE INVENTION

Figure 1A:
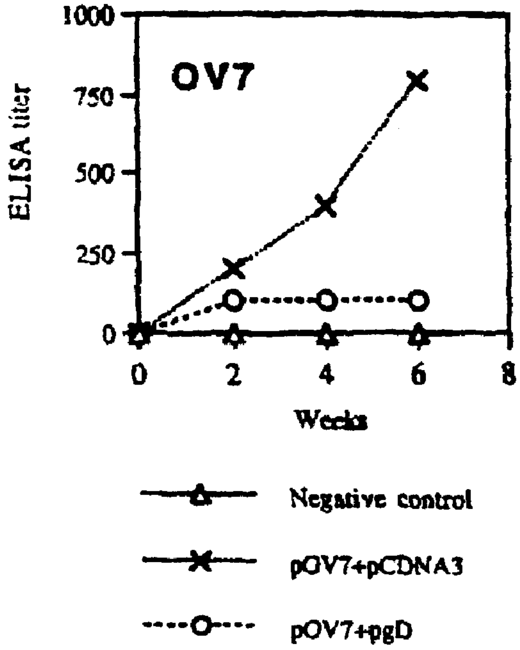
FIGS. 1A-1D show data from experiments described in the Example in which immune responses were compared from animals injected with gene constructs that encoded an immunogenic protein and a control vector or a construct that encoded gD protein.

As used herein, the terms "protein" and "polypeptide" are used interchangeably and intended to refer to proteinaceous compounds including proteins, polypeptides and peptides.

As used herein, gD refers to glycoprotein D from either human herpes simplex virus 1 (HSV-1) or human herpes simplex virus 2 (HSV-2). In preferred embodiments, gD is derived from HSV-1.

As used herein, the term "individual" refers to the vertebrate targeted for use of the present invention. Examples of "individuals" contemplated by the present invention include but are not limited to humans, higher order primates, canines, felines, bovines, equines, ovines, porcines, avians, and other mammals.

As used herein, the term "immunogenic vector" relates to a vector which elicits an immune response. Examples of immunogenic vectors include, but are not limited to viral and bacterial vectors. Some embodiments of the present invention relate to methods where the vector administered to the individual is viral. Examples of viral vectors include but are not limited to adenovirus, adenovirus associated virus, vaccinia virus, and SV40 virus. In a preferred embodiment, the vector is adenovirus. Some embodiments of the present invention relate to methods where the vector administered to the individual is bacterial. Examples of bacterial vectors include but are not limited to Salmonella, mycobacterium and BC. Examples of immunogenic vectors which are useful in gene therapy and which can be adapted to the present invention include recombinant adenoviral vectors which are described in U.S. Pat. Nos. 5,756,283 and 5,707,618, which are each incorporated herein by reference As used herein, the term "desired polypeptide" refers to the polypeptide for which gene therapy is desired. Examples of "desired polypeptides" include human and non-human polypeptides useful as a therapeutic or compensating protein in gene therapy regimens.

As used herein, the term "therapeutic protein" is meant to refer to proteins whose presence confers a therapeutic benefit to the individual.

As used herein, the term "compensating protein" is meant to refer to proteins whose presence compensates for the absence of a fully functioning endogenously produced protein due to an absent, defective, non-functioning or partially functioning endogenous gene.

In some of the embodiments of the invention that relate to gene therapy, the gene constructs contain either compensating genes or genes that encode therapeutic proteins. Examples of compensating genes include: the gene which encodes dystrophin, the gene to compensate for the defective gene in patients suffering from cystic fibrosis, the gene which encodes insulin, the gene to compensate for the defective gene in patients suffering from ADA, and the gene encoding Factor VIII. Examples of genes encoding therapeutic proteins include genes which encodes erythropoietin, interferon, LDL receptor, GM-CSF, IL-2, IL-4 and TNF. Additionally, genetic constructs which encode single chain antibody components which specifically bind to toxic substances can be administered.

In some preferred embodiments, the dystrophin gene is provided as part of a mini-gene and used to treat individuals suffering from muscular dystrophy. In some preferred embodiments, a mini-gene which contains coding sequence for a partial dystrophin protein is provided. Dystrophin abnormalities are responsible for both the milder Becker's Muscular Dystrophy (BMD) and the severe Duchenne's Muscular Dystrophy (DMD). In BMD dystrophin is made, but it is abnormal in either size and/or amount. The patient is mild to moderately weak. In DMD no protein is made and the patient is chair-bound by age 13 and usually dies by age 20. In some patients, particularly those suffering from BMD, partial dystrophin protein produced by expression of a mini-gene delivered according to the present invention can provide improved muscle function.

In some preferred embodiments, genes encoding IL-2, IL-4, interferon or TNF are delivered to tumor cells which are either present or removed and then reintroduced into an individual. In some embodiments, a gene encoding gamma interferon is administered to an individual suffering from multiple sclerosis.

In some preferred embodiments, the desired polypeptide is encoded by a gene encoding human growth hormone.

As used herein, the term "administration" refers to the delivery of polypeptides to an individual. "Administration" refers to the delivery of nucleic acids which encode polypeptides and also the delivery of polypeptides to the individual. The term includes, but is not limited to delivery routes including intramuscularly, intravenously, intranasally, intraperatoneally, intradermally, intrathecally, intravenitricularly, subcutaneously, transdermally or topically or by lavage. Modes of administration contemplated by this invention include but are not limited to the use of a syringe, intravenous line, transdermal patch, or needleless injector.

The present invention provides improved gene therapy vectors that employ one of the weapons that the HSV virus uses to evade and undermine an infected individual's immune system: the gD protein and/or a nucleic acid molecule that encodes it. Armed with this HSV-derived weapon, gene therapy vectors can be made more effective by reducing an individual's immune response against them. Moreover, the present invention uses the HSV gD protein and/or a nucleic acid molecule that encodes it to treat individuals who have diseases and conditions associated with undesirable immune responses.

The present invention arises from the surprising discovery that the delivery of gD polypeptide suppresses cellular immune responses. Accordingly, when delivered in the context of a gene therapy protocol, gD decreases the immune response directed at the gene therapy vector and cells infected by the same resulting in an increase in the efficacy of the gene therapy protocol. When delivered to an individual who has a disease or condition associated with an undesirable immune response such as an inflammatory or autoimmune disease or tissue or organ transplant, gD decreases the immune response. This immunosuppressive activity of gD makes it particularly suited for use in gene therapy since coding sequences that encode gD can be included in the gene therapy constructs themselves. In addition, this immunosuppressive activity of gD makes it an attractive alternative to other immunesuppressive therapies such as steroids in the treatment of autoimmune diseases.

The amino acid sequence of gD and the DNA sequence that encodes gD are disclosed in Genbank Accession Nos.: E0311—DNA encoding surface protein gD of herpes simplex virus type 1 (HSV-1) Miyarna strain; E03023—DNA encoding surface protein gD of HSV-1; E00402—Herpes simplex virus-1(HSV-1) glycoprotein D (gD) gene; E00401—Herpes simplex virus-1 (HSV-1) glycoprotein D (gD) gene; E00400—Herpes simplex virus-2 (HSV-2) glycoprotein D (gD) gene; E00395—Herpes simplex virus-1 (HSV-1) glycoprotein D (gD) gene; E00394—Herpes simplex virus-2 (HSV-2) glycoprotein D (gD) gene; K01408—Herpes simplex virus type 2 (HSV-2) glycoprotein D (gD-2) gene and flanks; and J02217—HSV1 glycoprotein D gene, which are each incorporated herein by reference as are the references reported with and corresponding to the Genbank Accession numbers. U.S. Pat. Nos. 5,958,895, 5,583,028 and 5,955,088, which are each incorporated herein by reference, disclose isolated gD protein or nucleic acid molecules that encode gD protein.

Functional fragments of gD are those truncated forms of gD protein which retain immunosuppressive activity. Functional fragments are preferably about 5 amino acids, more preferably 10 or more and more preferably 25 or more. Functional fragments can be identified routinely by comparing the immunosuppressive activity of fragments of gD with a negative control. A reduction in immune responses in the presence of a fragment of gD indicates that the fragment is a functional fragment.

One aspect of the present invention relates to methods of delivering a desired polypeptide to an individual comprising administering to the individual an immunogenic vector comprising a nucleic acid encoding the desired polypeptide operably linked to regulatory elements in combination with either the gD polypeptide, or a functional fragment thereof, or a nucleic acid encoding gD, or a functional fragment thereof operably linked to regulatory elements, or a combination thereof. According to one aspect of the invention, gD protein or a functional fragment thereof is delivered to an individual in combination with the delivery of an immunogenic vector for delivering the coding sequence of a desired protein in a gene therapy protocol. The gD may be delivered as a protein or a functional fragment thereof or as a nucleic acid molecule with the coding sequence for gD protein or a functional fragment thereof or any combination thereof. The gD may be delivered in the same formulation as the gene therapy vector or separately. The gD may be delivered simultaneously, prior to or subsequent to delivery of the gene therapy vector. In some preferred embodiments, the immunogenic vector comprises a nucleic acid molecule with the coding sequence for gD protein or a functional fragment thereof. In some preferred embodiments, the immunogenic vector comprises gD protein or a functional fragment thereof. In some preferred embodiments, the immunogenic vector comprises a nucleic acid molecule with the coding sequence for gD protein and/or a functional fragment thereof and gD protein and/or a functional fragment thereof itself. Once delivered to the individual, the nucleic acid encoding the desired polypeptide is expressed and the desired polypeptide is synthesized within the individual. The presence of the gD protein, either delivered as a protein or as a nucleic acid molecule "prodrug" which is expressed inhibits the immune response directed at the immunogenic vector.

The present invention provides improved gene therapy compositions and methods. Through gene therapy, polypeptides which are either absent, produced in diminished quantities, or produced in a mutant form in an individual may be replaced using a vector comprising a nucleic acid encoding the desired polypeptide. The desired polypeptide compensates for the lack of the desired polypeptide. Upon administration of the vector to the individual, the individual generates an immune response against the vector. The delivery of gD, either a protein or as a nucleic acid molecule "prodrug", in combination with the gene therapy vector that encodes the desired polypeptide inhibits the immune response directed at the immunogenic vector and therefore increases the efficacy of the gene therapy treatment.

The present invention also provides a method of treating individuals suffering from diseases and conditions characterized by undesirable immune responses such as autoimmune/inflammatory diseases and condition and organ/tissue/cell transplantation procedures. According to the invention, methods of treating an individual with a disease or condition associated with an undesirable immune response comprise administering to the individual gD protein or a functional fragment thereof or a nucleic acid encoding gD protein or a functional fragment thereof or a combination of two or more of the same. When a nucleic acid encoding gD protein or a functional fragment thereof is delivered to an individual, the coding sequence is operably linked to regulatory elements.

The gD may be delivered as a protein or a functional fragment thereof or as a nucleic acid molecule with the coding sequence for gD protein or a functional fragment thereof or any combination thereof. In some embodiments, the gD is delivered as a nucleic acid molecule with the coding sequence for gD protein and/or a functional fragment thereof. In some embodiments, the gD and/or a functional fragment thereof is delivered as a protein. Once delivered to the individual, the presence of the gD protein, either delivered as a protein or produced by the expression of the nucleic acid molecule that encodes it, inhibits the undesirable immune response.

According to some embodiments of the present invention, methods are provided for treating individuals suffering from autoimmune diseases and disorders. T cell mediated autoimmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases.

According to some embodiments of the present invention, methods are provided for treating individuals who require immunosuppression such as those undergoing transplantation procedure including cell, tissue and organ transplants. In such instances rejection of the transplanted material is reduced and the severity or incidence of side effects such as graft versus host disease may be lessened.

According to other embodiments, immune suppression can be induced to prevent damage resulting from inflammation. For example, following spinal cord injuries, a cascade of events leads to inflammation of the spinal cord and surrounding tissues. Use of the present invention may both inhibit inflammation of the spinal cord and associated problems and allow delivery of a therapeutic polypeptide to the individual. For instance, if an axonal guidance protein is the desired polypeptide, use of the present invention may both inhibit the inflammation of the spinal cord and stimulate axonal regrowth.

As discussed above, in some embodiments, gD is delivered alone and in some embodiments, gD is delivered in combination with a gene therapeutic including immunogenic vectors.

In some embodiments of the present invention, a combination of one or more of gD, a functional fragment thereof, a nucleic acid encoding gD, or a nucleic acid encoding a functional fragment of gD is administered to a patient.

In some embodiments of the present invention, gD or a functional fragment thereof is administered as a protein. In some embodiments, the gD or a functional fragment thereof is administered to the individual in the same formulation as the nucleic acid encoding the desired polypeptide. In other embodiments, the gD or a functional fragment thereof is administered to the individual in a separate formulation than the nucleic acid encoding the desired polypeptide. In some embodiments, the formulation containing the gD or a functional fragment thereof is administered to the individual at the same time as the formulation containing the nucleic acid encoding the desired polypeptide. In some embodiments, gD or a functional fragment thereof is delivered as a protein incorporated within an immunogenic vector.

In some embodiments of the present invention, a nucleic acid that encodes gD or a functional fragment thereof is administered. In some embodiments of the present invention, the desired polypeptide is encoded by a first nucleic acid while the gD or a functional fragment thereof is encoded by a second nucleic acid. In some embodiments, the nucleic acid that encodes gD or a functional fragment thereof is administered to the individual in the same formulation as the nucleic acid encoding the desired polypeptide. In other embodiments, the nucleic acid that encodes gD or a functional fragment thereof is administered to the individual in a separate formulation than the nucleic acid encoding the desired polypeptide. In some embodiments, the formulation containing the nucleic acid that encodes gD or a functional fragment thereof is administered to the individual at the same time as the formulation containing the nucleic acid encoding the desired polypeptide. In a preferred embodiment of the present invention, the nucleic acid that encodes gD or a functional fragment thereof and the desired polypeptide are encoded by the same nucleic acid which is a genome of an immunogenic vector. In some embodiments, the nucleic acid that encodes gD or a functional fragment thereof is administered free of an immunogenic vector that encodes a desired polypeptide.

In some embodiments, the gD coding sequence is delivered separate from or free of an immunogenic vector. Compositions and methods for delivering proteins to cells by direct DNA administration have been reported using a variety of protocols. Examples of such methods are described in U.S. Pat. Nos. 5,593,972, 5,739,118, 5,580,859, 5,589,466, 5,703,055, 5,622,712, 5,459,127, 5,676,954, 5,614,503, and PCT Application PCT/US95/12502, which are each incorporated herein by reference. Compositions and methods for delivering proteins to cells by direct DNA administration are also described in PCT/US90/01515, PCT/US93/02338, PCT/US93/048131, and PCT/US94/00899, which are each incorporated herein by reference. In addition to the delivery protocols described in those applications, alternative methods of delivering DNA are described in U.S. Pat. Nos. 4,945,050 and 5,036,006, which are both incorporated herein by reference. Nucleic acid molecules can also be delivered using liposome-mediated DNA transfer such as that which is described in U.S. Pat. Nos. 4,235,871, 4,241,046 and 4,394,448, which are each incorporated herein by reference.

Formulations comprising an immunogenic vector comprising the nucleic acid having a sequence encoding the desired polypeptide are made up according to the mode and site of administration. Such formulation is well within the skill in the art. In addition to nucleic acids and optional polypeptides, the formulation may also include buffers, excipients, stabilizers, carriers and diluents.

The pharmaceutical composition comprising gD protein or a fragment thereof and a pharmaceutically acceptable carrier or diluent may be formulated by one having ordinary skill in the art with compositions selected depending upon the chosen mode of administration. Suitable pharmaceutical carriers are described in the most recent edition of *Remington's Pharmaceutical Sciences*, A. Osol, a standard reference text in this field which is incorporated herein by reference.

For parenteral administration, the gD protein can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions comprising gD protein, or fragments thereof may be administered by any means that enables the active agent to reach the agent's site of action in the body of a mammal. Because proteins are subject to being digested when administered orally, parenteral administration, i.e., intravenous, subcutaneous, intramuscular, would ordinarily be used to optimize absorption.

The dosage administered varies depending upon factors such as: pharmacodynamic characteristics; its mode and route of administration; age, health, and weight of the recipient; nature and extent of symptoms; kind of concurrent treatment; and frequency of treatment. Usually, a daily dosage of gD protein can be about 0.1 to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Another aspect of the present invention relates to pharmaceutical compositions that comprise a nucleic acid molecule that encodes gD and a pharmaceutically acceptable carrier or diluent. According to the present invention, genetic material that encodes gD protein is delivered to an individual in an expressible form. The genetic material, DNA or RNA, is taken up by the cells of the individual and expressed. gD that is thereby produced can inhibit immune responses, either those directed at an immunogenic vector or another undesirable immune response such as those associated with autoimmune and inflammatory disease and conditions and transplantation procedures. Thus, pharmaceutical compositions comprising genetic material that encodes gD are useful in the same manner as pharmaceutical compositions comprising gD protein. gD or nucleic acid molecule with a gD coding sequence may be incorporated into an immunogenic vector.

Nucleotide sequences that encode gD protein operably linked to regulatory elements necessary for expression in the individual's cell may be delivered as pharmaceutical compositions using a number of strategies which include, but are not limited to, either viral vectors such as adenovirus or retrovirus vectors or direct nucleic acid transfer. Methods of delivering nucleic acids encoding proteins of interest using viral vectors are widely reported. A recombinant viral vector such as a retrovirus vector or adenovirus vector is prepared using routine methods and starting materials. The recombinant viral vector comprises a nucleotide sequence that encodes gD. Such a vector is combined with a pharmaceutically acceptable carrier or diluent. The resulting pharmaceutical preparation may be administered to an individual. Once an individual is infected with the viral vector, gD is produced in the infected cells.

Alternatively, a molecule which comprises a nucleotide sequence that encodes gD can be administered as a pharmaceutical composition without the use of infectious vectors. The nucleic acid molecule may be DNA or RNA, preferably DNA. The DNA molecule may be linear or circular, it is preferably a plasmid. The nucleic acid molecule is combined with a pharmaceutically acceptable carrier or diluent.

According to the invention, the pharmaceutical composition comprising a nucleic acid sequence that encodes gD protein may be administered directly into the individual or delivered ex vivo into removed cells of the individual which are reimplanted after administration. By either route, the genetic material is introduced into cells which are present in the body of the individual. Preferred routes of administration include intramuscular, intraperitoneal, intradermal and subcutaneous injection. Alternatively, the pharmaceutical composition may be introduced by various means into cells that are removed from the individual. Such means include, for example, transfection, electroporation and microprojectile bombardment. After the nucleic acid molecule is taken up by the cells, they are reimplanted into the individual.

The pharmaceutical compositions according to this aspect of the present invention comprise about 1 ng to 10 mg of nucleic acid in the formulation; in some embodiments, about 0.1 to about 2000 micrograms of DNA. In some preferred embodiments, the pharmaceutical compositions contain about 1 to about 1000 micrograms of DNA. In some preferred embodiments, the pharmaceutical compositions contain about 1 to about 500 micrograms of DNA. In some preferred embodiments, the pharmaceutical compositions contain about 25 to about 250 micrograms of DNA. Most preferably, the pharmaceutical compositions contain about 100 micrograms DNA.

The pharmaceutical compositions according to this aspect of the present invention are formulated according to the mode of administration to be used. One having ordinary skill in the art can readily formulate a nucleic acid molecule that encodes GD. In cases where injection is the chosen mode of administration, a sterile, isotonic, non-pyrogenic formulation is used. Generally, additives for isotonicity can include sodium chloride, dextrose, mannitol, sorbitol and lactose. Isotonic solutions such as phosphate buffered saline are preferred. Stabilizers include gelatin and albumin.

Regulatory elements for nucleic acid expression include promoters, initiation codons, stop codons, and polyadenylation signals. It is necessary that these regulatory elements be operably linked to the sequence that encodes the desired polypeptides and optionally the GD polypeptide and that the regulatory elements are operable in the individual to whom the nucleic acids are administered. For example, the initiation and termination codons must be in frame with the coding sequence. Promoters and polyadenylation signals used must also be functional within the cells of the individual.

Examples of promoters useful to practice the present invention include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metallothionein.

Examples of polyadenylation signals useful to practice the present invention include but are not limited to SV40 polyadenylation signals and LTR polyadenylation signals. In particular, the SV40 polyadenylation signal which is in pCEP4 plasmid (Invitrogen, San Diego Calif.), referred to as the SV40 polyadenylation signal, is used.

EXAMPLE

Figure 1B:
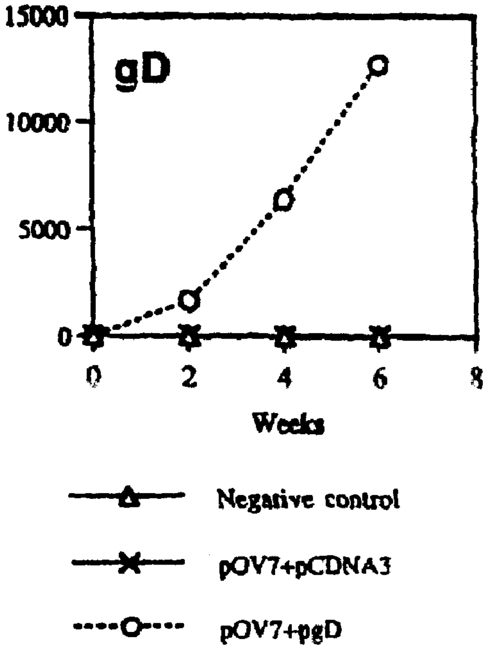
Figure 1C:
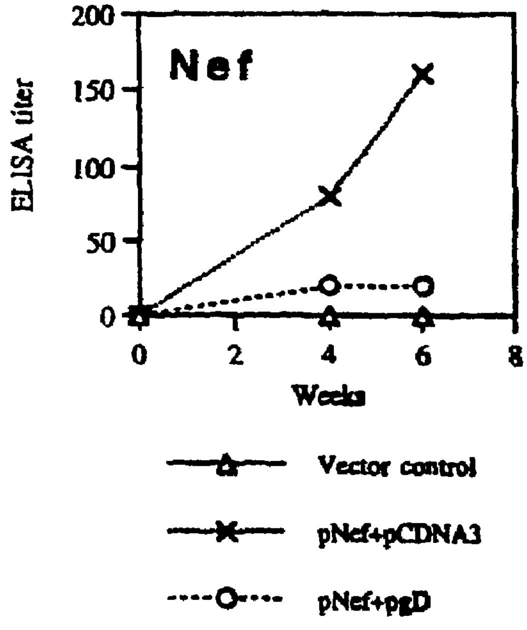
Figure 1D:
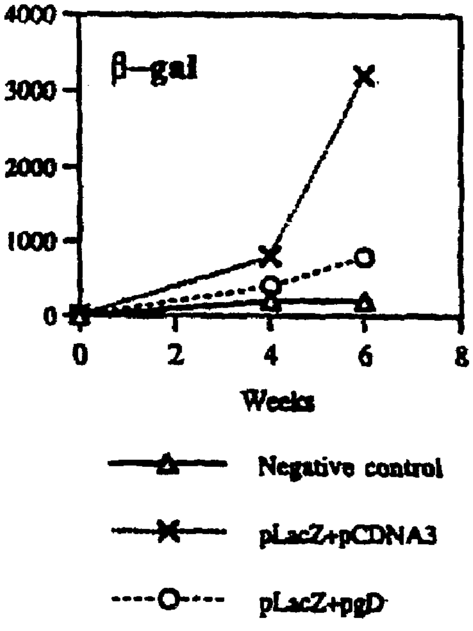

Animals were immunized by bupivacaine facilitated DNA vaccination using various combinations of gene constructs as shown in FIGS. 1A-1D. In each of FIGS. 1A, 1C and 1D, co-administration of gD constructs resulted in reduced immune responses against the antigen encoded by the other gene construct administered. FIG. 1B shows an anti-gD response. These data indicate that co-administration of gD-encoding constructs with a second construct that encodes a second immunogenic protein reduces the immune response against the second immunogenic protein.

The foregoing examples are meant to illustrate the invention and are not to be construed to limit the invention in any way. Those skilled in the art will recognize modifications that are within the spirit and scope of the invention. All references cited herein are hereby incorporated by reference in their entirety.

We claim:

1. A method for suppressing an immune response in an individual in need of such treatment comprising identifying said individual and administering to said individual in an amount sufficient to inhibit an undesirable immune response a nucleic acid molecule encoding gD protein operably linked to regulatory elements; wherein said gD protein is HSV-2 gD protein.

2. The method of claim 1 wherein the individual has an autoimmune/inflammatory disease or condition.

3. A method for suppressing an immune response in an individual in need of such treatment comprising identifying said individual and administering to said individual in an amount sufficient to inhibit an undesirable immune response a nucleic acid molecule encoding gD protein operably linked to regulatory elements; wherein said gD protein is selected from the group consisting of: HSV-1 gD protein and HSV-2 gD protein, wherein the individual is undergoing or has undergone a cell, tissue or organ transplant procedure.

* * * * *

UNITED STATES PATENT AND TRADEMARK OFFICE

CERTIFICATE OF CORRECTION

PATENT NO. : 7,569,218 B2
APPLICATION NO. : 10/333802
DATED : August 4, 2009
INVENTOR(S) : Weiner et al.

It is certified that error appears in the above-identified patent and that said Letters Patent is hereby corrected as shown below:

On the title page,

[*] Notice: Subject to any disclaimer, the term of this patent is extended or adjusted under 35 USC 154(b) by (608) days Delete the phrase “by 608 days” and insert -- by 989 days --

Signed and Sealed this

Sixth Day of April, 2010

David J. Kappos
*Director of the United States Patent and Trademark Office*